(12) United States Patent
Genovese et al.

(10) Patent No.: US 9,023,291 B2
(45) Date of Patent: May 5, 2015

(54) COLORIMETRIC DETECTOR

(71) Applicant: U.S. Army Research Development and Engineering Command, APG, MD (US)

(72) Inventors: James A. Genovese, Street, MD (US); Edward Rychwalski, III, Abingdon, MD (US); Kevin Ridgley, Newark (DE); Richard Kreis, Bel Air, MD (US); Kevin M Murphy, Bel Air, MD (US)

(73) Assignee: The United States of America as Represented by the Secretary of The Army, Washington, DC (US)

( * ) Notice: Subject to any disclaimer, the term of this patent is extended or adjusted under 35 U.S.C. 154(b) by 42 days.

(21) Appl. No.: 13/658,222

(22) Filed: Oct. 23, 2012

(65) Prior Publication Data
US 2014/0065030 A1    Mar. 6, 2014

Related U.S. Application Data

(60) Provisional application No. 61/551,134, filed on Oct. 25, 2011.

(51) Int. Cl.
*G01N 21/75* (2006.01)
*G01N 33/22* (2006.01)
(Continued)

(52) U.S. Cl.
CPC .............. *G01N 33/227* (2013.01); *G01N 21/78* (2013.01); *B01L 2200/16* (2013.01); *G01N 2001/028* (2013.01); *B01L 2300/0887* (2013.01); *B01L 2200/0673* (2013.01); *B01L 2300/0816* (2013.01); *B01L 2300/044* (2013.01); *B01L 3/5027* (2013.01); *B01L 3/5085* (2013.01); *G01N 21/63* (2013.01); *B01L 3/0293* (2013.01); *G01N 31/22* (2013.01); *G01N 31/227* (2013.01)

(58) Field of Classification Search
CPC ................... B01L 2200/16; B01L 2300/0816; B01L 230/0887; B01L 2300/044; B01L 3/5027; B01L 2200/0673; B01L 3/0293; B01L 3/5085; G01N 2001/028; G01N 21/78; G01N 33/227; G01N 21/63
USPC ......... 422/400, 401, 420, 421, 422, 423, 424, 422/425, 426, 427, 428, 429, 68.1, 82.05, 422/82.06; 436/164, 169, 170
See application file for complete search history.

(56) References Cited

U.S. PATENT DOCUMENTS 3,689,224 A * 9/1972 Agnew et al. ................. 422/413
5,750,184 A * 5/1998 Imburgia .................... 427/2.13
(Continued)

OTHER PUBLICATIONS

Rozin et al, "Colorimetric detection of urea nitrate: The missing link", Forensic Science International, vol. 208, Issues 1-3, May 20, 2011, pp. 25-28.*

*Primary Examiner* — Dennis M White
(74) *Attorney, Agent, or Firm* — Ulysses John Biffoni

(57) ABSTRACT

The present invention is directed toward a colorimetric detection kit comprising a unit containing chemical reagents and a sample collector for collecting a sample analyte from a surface and a separate unit for visualizing a possible reaction of the chemical reagent and sample, the unit holding the chemical reagents and sample collector being placeable on the visualization unit, whereby when the chemical reagents are released, they are directed onto the sample collector for reaction and the reacted reagents absorbed on a visualization media, such that the presence of a specified analyte in the sample results in a color change in the visualization media.

15 Claims, 5 Drawing Sheets

(51) Int. Cl.
*G01N 31/22* (2006.01)
*G01N 21/78* (2006.01)
*G01N 1/02* (2006.01)
*B01L 3/00* (2006.01)
*G01N 21/63* (2006.01)
*B01L 3/02* (2006.01)

(56) References Cited

U.S. PATENT DOCUMENTS 8,889,421 B1 * 11/2014 Ouellette et al. ............. 436/110
2008/0112848 A1 * 5/2008 Huffstodt et al. ............ 422/68.1
2008/0274014 A1 * 11/2008 Jumonville et al. ............ 422/57

* cited by examiner

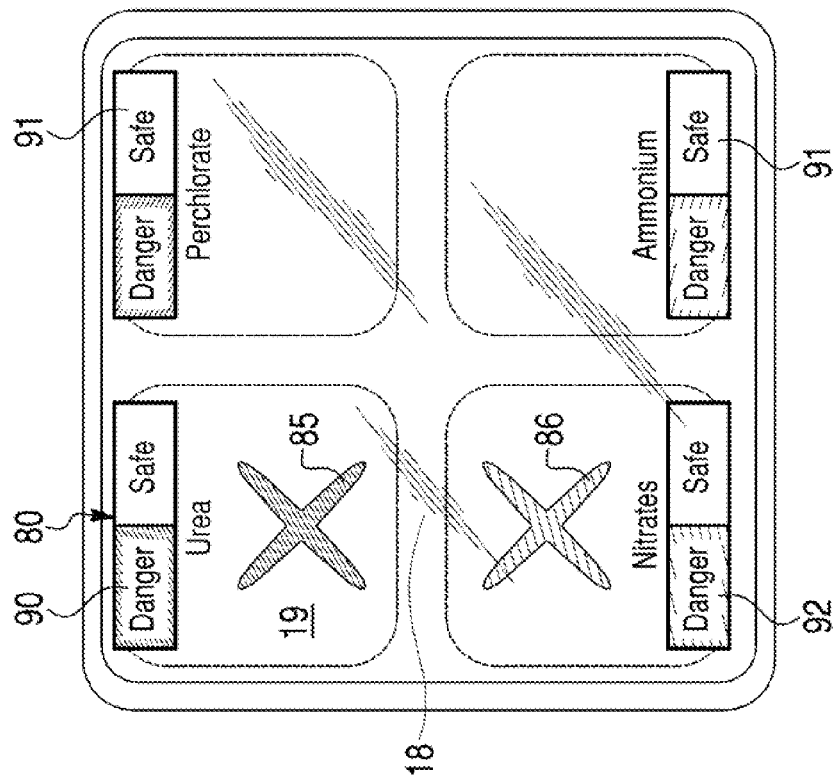
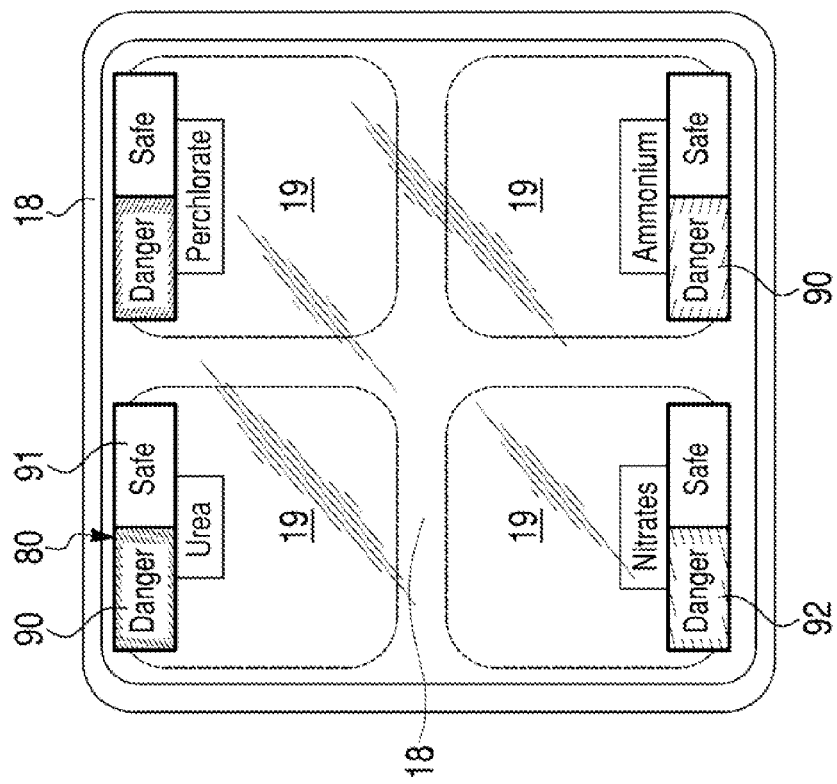

COLORIMETRIC DETECTOR

GOVERNMENT INTEREST

The invention described herein may be manufactured, used and licensed by or for the U.S. Government.

FIELD OF INVENTION

The present invention relates to a portable detector that collects and detects liquid or solid phase analytes in samples collected from the environment.

BACKGROUND

Most portable sample detectors only identify one analyte for a given singular device. These analyte detections often rely upon the users' ability to select the correct device for a specific analyte. During sampling, users may not be fully knowledgeable of all of the analytes that can possibly be present in the environment. This situation can lead to longer detection times and prolonged durations in a hazardous environment, which may cause severe injuries or death. Additionally, low volatility and/or solid phase analytes (i.e. ammonium nitrate, perchlorate salts, urea, and urea nitrate) do not produce enough vaporous mass due to their inherently low volatilities and, thus, cannot be detected via traditional selective vapor phase sampling means (i.e. M256A2, JCAD). Therefore, there is a need for a multiplex method and a detection device that is relatively inexpensive to manufacture, which requires minimal training to rapidly and/or to simultaneously sample and detect multiple analytes in the environment.

SUMMARY OF THE INVENTION

The present invention can be characterized as a Colorimetric Homemade Explosive Detector (CHED), and is a collection/concentration sampler and detector of liquid or solid phase analytes from diverse environmental matrices, specifically explosive compounds for their precursors). The CHED can presumptively identify multiple explosive analytes of interest, which may consist of one or multiple chemical functional groups of a particular chemical or explosive compound. The CHED collects via a physical contact interaction between solids and liquids on a surface and a sampling/collector pad. The collector pad can move across an area to collect samples over a larger surface (with respect to the sampler's surface area) leading to increases in concentration of the analyte for trace analysis. The sampling pad is placed in a compact detection unit of the device. The detection unit of this invention includes a compact sampling and chemical unit juxtaposed and openable relative to the detection unit. The device provides a pathway between the sampling and chemical unit and the collector pad to provide visualization of any chemical reaction on the collector pad to determine the presence of a suspect analyte.

BRIEF DESCRIPTION OF THE DRAWINGS

For a fuller understanding of the nature and advantages of the present invention, reference should be made to the following detailed description read in the conjunction with the accompanying drawings.

FIGS. 6A and B illustrate the visualization media and backside of the colorimetric detection kit from FIG. 5, wherein labels designate the absence or presence of a specific analyte on the visualization media, FIG. 6A indicating an unspent DAVU, and FIG. 6B indicates a reacted DAVU.

DETAILED DESCRIPTION OF THE INVENTION

Figure 1:
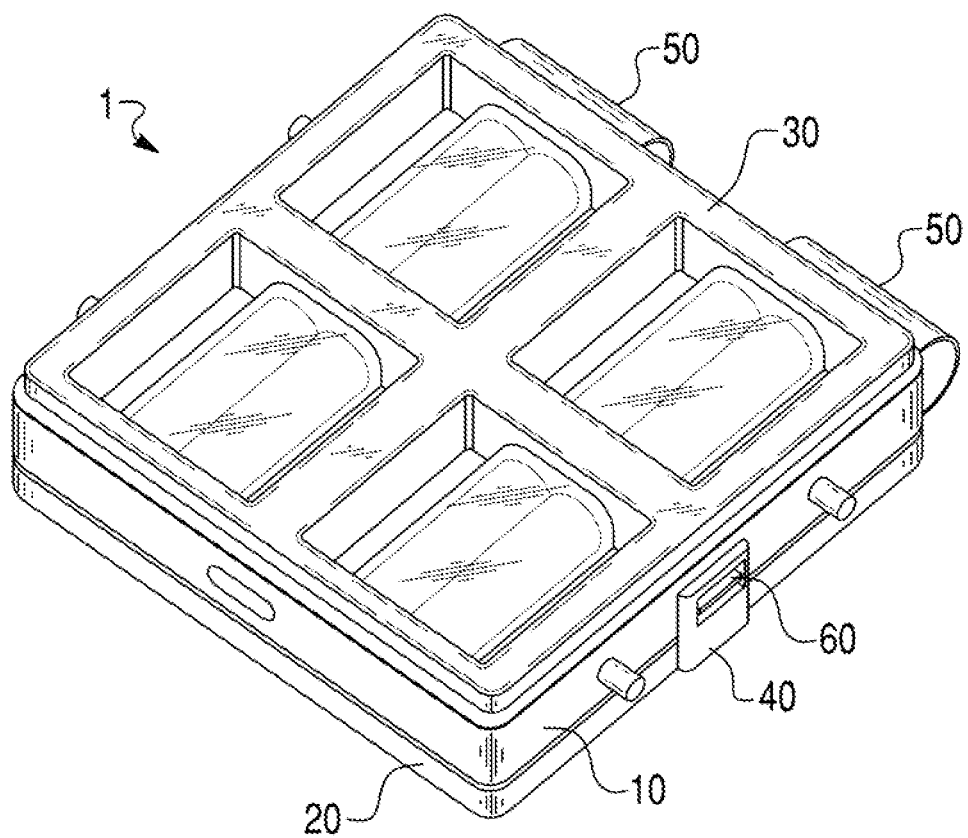
FIG. 1 is a perspective view of a fastened or closed colorimetric detection kit that has a detection and visualization unit ("DAVU") at the bottom, which is adjacent to and clipped onto a sampling and chemical unit ("SACU") on the top.
Figure 2:
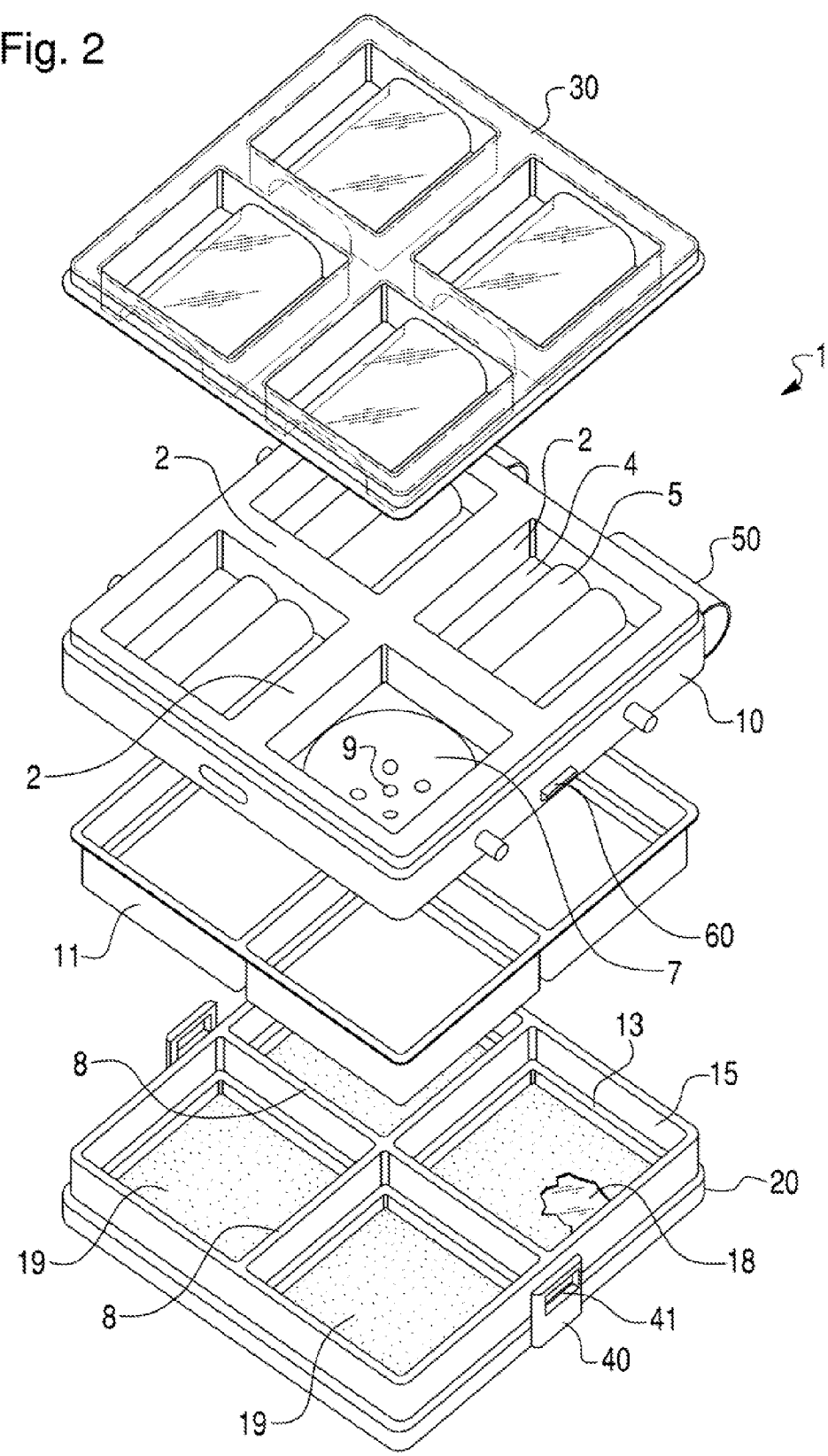
FIG. 2 is an exploded view of the components of the colorimetric detection kit from FIG. 1, wherein the bottom component is the DAVU that is comprised of detection and visualization cells ("DAVC"), the top component is the SACU comprised of chemical reagent cells "CRC" and a sample collector.

The present invention is directed toward a colorimetric detection kit and its use for collecting multiple samples and detecting liquid or solid analytes from these samples, which are obtained from diverse environmental matrices. As shown in FIGS. 1 and 2, the colorimetric detection kit 1 comprises a detection and visualization unit ("DAVU") 20, a sampling and chemical unit ("SACU") 10, and a protective cover 30 that overlays the SACU 10. A sample collector 11 is attached to and is part of the SACU. An attachment means comprising clips 40 with groove 41 on the side of unit 20, receives protrusion 60 extending from the side of unit 10 to fasten the SACU 10 to the DAVU 20, wherein the SACU 10 can be placed adjacent to and flush against the DAVU 20 to create a tight seal.

Figure 5:
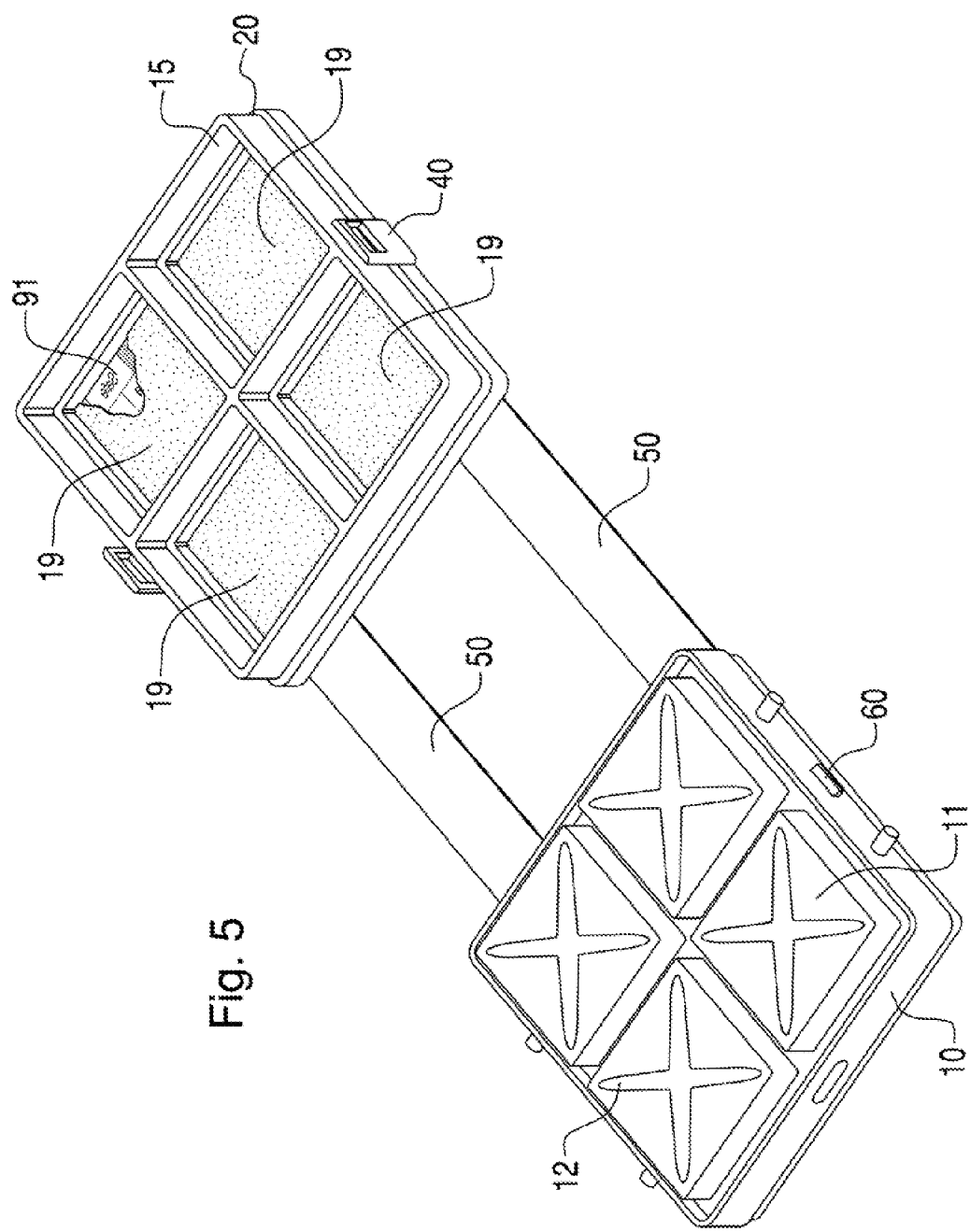
FIG. 5 illustrates a perspective view of an unfastened version of the colorimetric detection kit from FIG. 1, wherein the SACU is separated from the DAVU and ready for collection of samples.

The SACU 10 can be separated from DAVU 20 and remains attached thereto via a pair of flexible hinges 50, allowing the opening and closing of SACU 10 to DAVU 20, FIGS. 1, 2 and 5. The bias in hinges 50 tightly seals the SACU 10 to DAVU 20 to prevent any leakage of chemicals and provides for accurate reactions to take place in each visualization cell, as will be described below. The SACU 10 is comprised of multiple individually confined and equally sized chemical reagent cells ("CRC") 4. The DAVU is comprised of multiple individually confined and equally sized detection and visualization cells ("DAVC") 15. Each of the DAVC 15 contains a visualization media 19. The visualization media 19 is comprised of a flat absorbent pad. The absorbent pad can be transparent, white, or of any color that produces a stark contrast with the color) change induced by the presence of an analyte. The absorbent pad can be in the form of a filter paper, a silica gel paper, a cloth and a glass fiber disk, etc. The paper or cloth can, for example, be made of cotton yarn, cellulose fibers, rayon blend, borosilicate glass fiber with PVA binder, cellulose and synthetic blend with PVA binder, or cotton linter. The pad may or may not be coated with a sticky adhesive material or other support additives as needed, i.e., impregnated with an enzyme specific for urea hydrolysis. The preferred materials are cotton linter that is commercial available as Whatman® Absorbent Sinks, and cloth membrane that is commercially available as Dupont Sonatra® 8426. As will be discussed below, the visualization media 19 may also be the sampling or collection pad which collects samples from the environment. Each of the CRC 4 contains at least one chemical color detection reagent in ampoules 5. Very briefly, for colorimetric detection, the kit 1 is first unfastened and the collection pad 11 on the bottom of SAVU 10, as shown in FIG. 5, is pressed against a suspect surface. The kit is then fastened and the color detection reagents within each of the CRC 4 are released from their containers and directed downward onto the collection pad 11 for reaction with any suspect analyte and the reacted reagent is then directed onto and into the visualization media 19. The reacted reagents are absorbed by the visualization media 19, in each of the DAVC 15. The visualization media then indicates the color change in the presence of a specific analyte. The visualization media 19 is viewable through transparent bottom surface 18 of DAVU 20.

Sampling and Chemical Unit (SACU)

Figure 3:
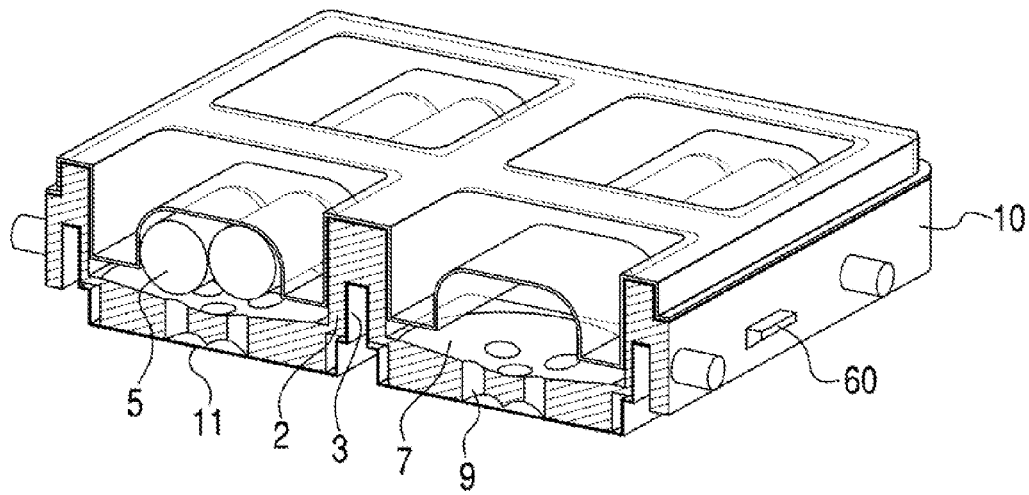
FIG. 3 illustrates a cutaway view of the SACU.

Referring to FIGS. 2 and 3, the sampling and chemical unit ("SACU") 10 is the top component of the colorimetric detection kit 1. The SACU 10 is comprised of multiple, individually confined and equally sized chemical reagent cells ("CRC") 4. Each of the CRC 4 houses at least one chemical reagent, carried in containers such as breakable ampoules 5. Below ampoules 5 is a directing sink 7, with apertures 9 that enable the chemical reagents to be released downward from the broken ampoules 5 to the sampling collector 11 and to DAVU 20. Beneath each of the sinks 7 is placed sample collector surface and pad 11. FIG. 5 illustrates sample collector 11, with a customized surface geometry to concentrate the samples collected and reagents in the form of a pattern. This pattern allows any positive detection to be readily visible by the user on the surface of the visualization media 19 of the DAVU 20, through transparent bottom surface 18.

The SACU 10 can be in the shape of a square, rectangle, circle, or any shape that enables the colorimetric kit 1 to be handheld and portable. Preferably, the SACU 10 has a square shape. Each of the CRC 4 can have a geometric shape compatible with the shape of the SACU 10. Again, as shown in FIGS. 1 and 2, each CRC 4 has a square shape. Each square CRC 4 can have a surface area of approximately 0.5 to 2 square inches, and preferably 1 square inch. The SACU 10 and the CRC 4 are preferably made of an inert lightweight plastic material selected from polyethylene, polypropylene, polystyrene, polyvinyl chloride, polytetrafluoroethylene and mixtures thereof. Polypropylene is preferred. The SACU 10 may include two to ten CRC 4, preferably four to eight CRC 4, and most preferably four CRC 4 that are arranged in a square so that the SACU 10 can be readily hand-held. The bottom of each of the CRC 4 is in the form of a concave sink 7, which sink 7 also includes at least one draining channel 9. A plurality of channels 9 are preferred. At least one chemical reagent container such as in the form of ampoules 5 is anchored within each of the CRC 4 and above the concave sink 7. The sample collector or pad 11 is attached such as by an adhesive to the bottom of sink 7, see FIG. 3.

The chemical color detection reagent in each container or ampoule 5 is in the form of a liquid or powdered solid that is directed through the draining channels 9, in sink 7, without clogging the channels. The chemical reagent is contained within a container 5 that is easily breakable, and yet, provides long-term stable storage of the reagent when the kit 1 is not in use. The containers shown in the Figures are in the form of ampoules 5 that are formed from glass or fit) breakable plastics, which are non-reactive with the reagent materials contained therein. The ampoules 5 can be hermetically sealed to prevent loss of activity and protected from UV photosynthesis to maintain activity. Ampoules 5 that are located within each of the CRC 4 may also be labeled with numbers or letters to indicate the appropriate order of release events.

The chemical color detection reagents can be made from any flowable chemicals known in the art to provide color reactions upon their interaction with specific analytes. More than one chemical can be incorporated into a reagent. While not intended to be limiting, the kit 1 and the chemical reagents contained therein are particularly useful in detecting explosive compounds or precursors of such materials. For example, in the detection of nitrate, a mixture of phosphoric acid ($H_3PO_4$) and di-n-propylamine ("DPA") is used. Meanwhile, for the detection of ammonium, a Nessler's solution (a mixture of Potassium tetraiodomercurate (II) and potassium hydroxide) is used. Preferably, four sets of reagents are anchored within a SACU 10 for the purpose of detecting homemade explosives ("HME"), such that the colorimetric kit has four CRC 4 that are respectively designated to detect four main ingredients of HME: two fuels (ammonium and urea) and two oxidizers (perchlorate and nitrate). The colorimetric detection kit 1 of this configuration for detecting HME can be characterized as a colorimetric homemade explosive detector ("CHED"). Thus, kit 1 can include both a reagent for fuel and oxidizers, such that a positive test for both is a ready indication of an explosive.

The SACU 10 has partitions 2 to separate each of the CRC 4. The underside of partitions 2 are formed as interlocking channels or grooves 3, see FIG. 3. In a fastened or closed position, the grooves 3 fit snuggly onto the partitions 8 that divide each of the corresponding detection and visualization cells ("DAVC") 15, in DAVU 20, in order to create a tight seal to prevent leakage of chemical reagents and samples from one CRC 4 to another.

The sample collection surface 11 can be made of at least one material that holds a static charge and/or is rough in nature to increase the sample) collection efficiency as it is swiped across or pressed against a suspect surface. The sample collection surface 11 can be constructed of a fibrous and/or porous material or coated with absorptive materials specific to suspected analytes. Alternatively, the collection surface 11 can be wetted with a solvent, or include an adhesive compound to increase the liquid and solid sampling efficiency of the collection surface from the environment on which the collection surface is contacted. A useful embodiment employs an adhesive material (akin to that used on 3M sticky notes) on an inert and roughed cloth. The sample collection surface 11 and adhesive should be chemically inert to the analytes of interest. The adhesive can be selected from pressure sensitive adhesives such as acrylate-based polymers and bio-adhesives such as vegetable matter, starch (dextran), and natural resins or those from animals, e.g., casein or animal glue. The most preferred adhesive is 3M™ Repositionable Spray Adhesive 75. The sample collection surface 11 can include an adhesive on both opposing surfaces, one surface for effectively adhering the suspect sample thereto and the opposing surface to allow the collection surface 11 to be secured within the SACU 10 during sampling and testing with the reagent(s).

The sample collection surface or pad 11 may further include a customized surface geometry, as shown in FIG. 5. Specifically, the surface geometry of sample collector 11 includes a recess 12 or set of recesses 12, such as in the form of a star, a cross, a check mark or any geometric shape that concentrates the sample within the recesses 12, and allows any color change on the collection surface 11 to be reproduced in the visualization media 19, in the shape of the recess 12. This may allow for better contrast with the color of surface media 19, and provide easier detection of a positive presence of an analyte in the sample being tested. This is particularly useful if the user is encumbered with physical protection gear, including protective goggles or masks.

The SACU 10 further includes a protective cover 30 that overlays the entire unit, and aids in holding the ampoules 5 in place within each CRC 4. The cover 30 also confines the reagent after the ampoules 5 are broken, and protects) the user's fingers and hand or any other crushing device from pieces of the broken chemical containers 5 when the reagents are released from the containers 5 by the user. Cover 30 also provides the operator with a surface to help force the reagents into and through apertures 9 and onto the sample collection surface 11. The protective cover 30 may also include instructions (not shown) for each of the CRC 4, to designate each CRC 4 for a specific analyte. The instructions in the form of letters, numbers or some other logical symbol order, may impart a direct means to enable simple instructional direction as to the mechanical ampoule manipulative procedures required for the necessary detection procedures. Ampoules 5 located in one volume may be labeled with numbers or letters to further indicate the appropriate order of events, or the ampoules 5 within one volume could be further segregated into smaller volumes that are labeled as discussed above.

Detection and Visualization Unit (DAVU)

Figure 4:
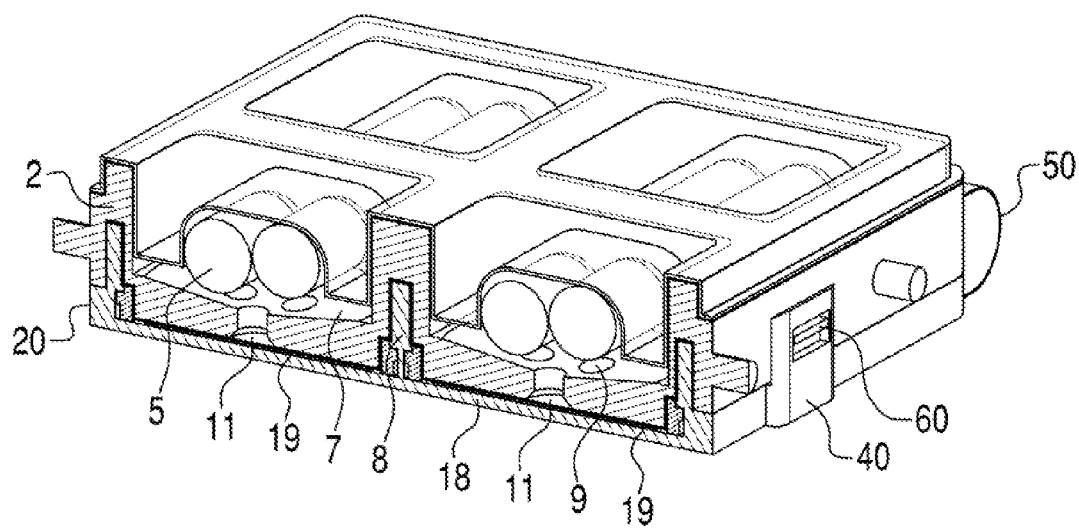
FIG. 4 illustrates a cutaway view of the fastened or closed colorimetric detection kit from FIG. 1.

Referring to FIGS. 2 and 4, the detection and visualization unit ("DAVU") 20 is the bottom component of the colorimetric detection kit 1. The DAVU 20 is comprised of multiple, individually confined and equally sized detection and visualization cells ("DAVC") 15. Each of the DAVC 15 houses a visualization media 19 on a transparent bottom surface 18. The visualization media 19 fits within each cell 15, and can be held in place by ridge 13, extending from the perimeter of each cell 15. The backside of bottom surface 18 associated with each of the DAVC 15 preferably contains visual cues or labels that help the operator determine whether the presence or absence of a specific analyte has been found. For example, the presence of a specific analyte can be designated in a label by a certain color. The operator can then compare the label color with the color formed in the visualization media 19, through bottom surface 18. This will be more fully described relative to FIGS. 6A and 6B below.

Each DAVC 15 can be in the shape of a square, rectangle, circle, or any shape that enables the colorimetric detection kit to be handheld and portable. Preferably, each DAVC 15 has a square shape. Thus, as described above for each CRC 4, DAVC 15 also has a surface area of approximately 0.5 to 2 square inches, and preferably 1 square inch. Importantly, each DAVC 15 has to be of the same dimensions and shape as the CRC 4, so that when the SACU 10 is folded over and fastened to the DAVU 20, the cells from both units can be locked and sealed as juxtaposed with one another to prevent reagent leakage and cross-contamination between adjacent cells. Each of the DAVC 15 and, in particular, bottom surface 18 is made of a transparent and lightweight material selected from acrylic (i.e. poly(methyl methacrylate), butyrate (i.e. cellulose acetate butyrate), lexan (i.e. polycarbonate), polypropylene and PETG (i.e. glycol modified polyethylene terphthalate), or the same material as CRC 4. A preferred material is polypropylene. The transparency of the selected material allows for a quick visual inspection of the colorimetric detection process. Furthermore, as for the CRC 4, the selected material should be semi-rigid and rugged, capable of slight sideways tension and torque, with the ability to be tossed around with little or no structural damage.

A DAVU 20 may include two to ten DAVC 15, preferably four to eight DAVC 15, and most preferably four DAVC 15 arranged in a square so that the DAVU 20 can be fit precisely and compactly with SACU 10 and be hand-held. Importantly, the number of the DAVC 15 should be the same as the number of the CRC 4, so that when the SACU 10 is folded over and fastened over the DAVU 20, the cells from both units are locked and sealed with one another to prevent reagent leakage and cross-contamination. Again, as shown in FIG. 3, each of the partitions 8, between cells 15, will fit within each groove 3 of partition 2 of each cell 4.

When the kit 1 is fastened after sample collection, the chemical reagents are released from ampoules 5, and the reagents are directed downward through apertures 9 and directed onto sample collector 11 for reaction. The reacted reagent is then wicked or absorbed by the visualization media 19. An appropriate color on media 19 indicates the presence of a specific analyte. The reagent containers or ampoules 5 can be opened in any sequence or timing to provide the desired reaction characteristics, i.e. one ampoule could be broken, its contents allowed to interact with the analyte, followed shortly with a second ampoule being broken, and its interaction with the now reacted analyte of interest. The reagent containers can also be opened simultaneously if so desired. Optionally, a small handheld device (not shown) could be provided to allow the user to crush multiple ampoules concurrently. This device could be designed such that when pressed up against the body of the ampoules, it crushes only those ampoules not positioned below open cavities in the device, and that so when rotated or repositioned into a predetermined alternative orientation, it is aligned such that subsequent ampoules can be crushed as necessary.

The backside of bottom surface 18 of each of the DAVC 15 can be labeled with visual cues which indicate the expected color of the visualization media 19, in the presence of a specific analyte. Referring to FIG. 6A, four pads of untreated visualization media 19 are shown through clear bottom surface 18. Four labels 80, each reciting the analyte being tested for and the colors 90 and 91 which indicate, respectively, the presence or absence of the analyte of interest are provided on the outside of bottom surface 18. For example, for the detection of ammonium, the pre-made Nessier's reagent will result in a yellow/orange/brown (concentration dependent) color in the presence of $NH_3$, as the ammonium reacts with the mercury in the reagent. Thus, the "Danger" label 90 for the "Ammonium" label will have a yellow/orange/brown color. For the detection of nitrate, diphenylamine in a strong acid (phosphoric acid) forms a dissolvable salt to produce a very dark (black) oxidation colorimetric response in the presence of nitrates. Thus, label 80 for "Nitrates" will include a "Danger" label portion 92 that is black. Each "Safe" label can be the background color of visualization media 19, or a reaction color that indicates the absence of the specific analyte that is being tested for. FIG. 6B illustrates the presence of "Urea" and "Nitrates". Thus, upon reaction and absorption of the reacted reagent from collector 11 in media 19, there resulted a color pattern 85 that matches the color in "Danger" label 90. Likewise, color pattern 86 on media 19 for "Nitrates" matches the color in "Danger" label 92. The visualization media 19 for "Perchlorate" and "Ammonium" remained uncolored, indicating the absence of the analytes as the reaction color matches the color of "Safe" label 91.

Method of Use

This invention is designed to collect and concentrate the analyte sample from the surrounding environment with a single device. After a protective adhesive cover (not shown) is removed from the surface of the sampling pad 11, for example, the sampling pad is ready to be brought into contact with the hazardous area of interest, see FIG. 5. The sampling pad 11 can be dipped or pressed into a liquid or onto a solid material or rubbed over a surface of an area of interest to increase the amount of analyte or area of interest sampled from. The SACU 10 is then closed over DAVU 20, as shown in FIG. 4. The ampoules 5 or reagent containers are opened by a mechanical crushing action by employing finger pressure or use of a hand held device in a uniform manner, as described above, so as to force the reagent liquid through the apertures 9, beneath the ampoules in sink 7, and directly onto sample collector 11. The reacted reagent will then be absorbed into visualization media 19. After a defined reaction and absorption waiting period, the detection areas of media 19 are visually or electronically inspected for a color change (infrared, visible, UV spectrum) or physical change (liberation of heat, foaming, fuming, smoking, chemiluminescence, luminescence, phosphorescence, and fluorescence). The preferred embodiment will employ the visual inspection of a color change employing the operator's visual modality. The individual detection areas colorimetric detections scheme can be employed individually or in a combinatorial fashion to detect or identify an analyte of interest or chemical category of interest as several or all at once. Although not preferred, it is possible to eliminate sample collector 11, and place a sample analyte collected by hand held means directly onto visualization media 19. Upon breakage of ampoule 5, the reagent will contract and react with the analyte on media 19 directly.

To determine if the proper color change even has occurred, the support area around the visualization media 19 will be colored and/or text labeled in a manner to represent a positive detection event, such as described for FIG. 6A. The color on the media surface 19 can be compared directly against the color indicators to assess or determine if the test is a positive or negative detection event, to include both positive and negative color outcomes, see FIG. 6B. In order for the user to be certain of the results, a color comparison chart will be integrally attached so negative and positive colorimetric results can be easily recognized by the user. This can be accompanied by a short step by step guide, in cases where ampoule fills must be liberated in a non-simultaneous fashion.

The kit of the present invention provides advantages over prior art detection devices; in that the improved kit allows multiple detection capabilities to analyze liquid and solid phase materials, such as fuel/oxidizer materials from a single sample, and a single handheld device. The kit allows sampling from a small or wide environment for one or more analytes, and provides a means for rapid concentration of such analytes, yielding lower detectable limits for such materials. The present kit is inexpensive to fabricate, is disposable, and has ease of use, requiring minimal training so that an unskilled operator can perform the detection process quickly and safely. Because the device is portable, relatively small in volume and light in weight, the kit can be easily transported and operated for sampling, detection and analysis. Because of the relativity small size of the kit, multiple kits can be configured in a relatively light weight travel box. The present kit requires no batteries or electrical power to operate.

The forgoing discussion discloses and describes merely exemplary embodiments of the present invention. One skilled in the art will readily recognize from such discussion, and from the accompanying claims, that various changes, modifications, and variations can be made therein without departing from the spirit and scope of the invention as defined in the following claims.

The invention claimed is:

1. A colorimetric detection kit for detecting analytes in a suspect sample from an environment, comprising:
 a detection and visualization unit (DAVU) comprised of four, individually confined cells each containing a visualization surface for receiving a reacted chemical reagent;
 a sampling and chemical unit (SACU) separate from and placeable adjacent to and juxtaposed against said DAVU, said SACU also comprised of four individually confined cells such that when said SACU is juxtaposed against said DAVU the individual cells of said SACU are juxtaposed against the individual cells of said DAVU, each of said cells of said SACU containing at least one chemical reagent reactive with said analytes, wherein said chemical reagents are contained in breakable containers within each cell of said SACU, and wherein said SACU includes one cell containing reagents useful for detecting urea, one cell containing reagents useful for detecting ammonium, one cell containing reagents useful for detecting perchlorate, and one cell containing reagents useful for detecting nitrate, and said SACU also having a sample collector positioned so as to be capable of receiving said chemical reagents and adjacent to said visualization surface when said SACU is placed against said DAVU; and
 wherein said sample collector includes an adhesive surface for effectively adhering suspect sample thereto in order to collect a sample from a surface, and wherein said visualization surface displays a color change when receiving said reacted chemical reagents in the presence of at least one suspect analyte.

2. The kit of claim 1, wherein each individual cell of said SACU contains a plurality of said breakable containers.

3. The kit of claim 1, wherein said DAVU and SACU are attached by a hinge that allows said SACU to be placed adjacent to and juxtaposed against said DAVU.

4. The kit of claim 1, wherein said SACU and DAVU contain complementary locking members to close and lock said SACU against said DAVU.

5. The kit of claim 1, wherein said SACU further includes a cover to maintain said breakable containers in said SACU.

6. The kit of claim 1, wherein said SACU contains a surface having apertures contained therein and situated below said breakable containers, said apertures directing said chemical reagents to said sample collector.

7. The kit of claim 6, wherein said surface having apertures is of a concave shape.

8. The kit of claim 1, wherein said sample collector has a sample collection surface containing a recessed pattern therein.

9. The kit of claim 8, wherein said recessed pattern is in the form of a star, cross or check mark.

10. The kit of claim 1, wherein the individual cells of said SACU interlock with the corresponding individual cells of said DAVU when said SACU is juxtaposed against and positioned adjacent to said DAVU, so that said cells are attached and sealed with one another to prevent leakage and cross-contamination.

11. The kit of claim 1, wherein said visualization surface is placed on a bottom surface of said DAVU.

12. The kit of claim 1, wherein said visualization surface is absorbent.

13. The kit of claim 11, wherein said bottom surface of said DAVU is transparent, and said change displayed on said visualization surface comprises a change of color in the presence of said at least one suspect analyte.

14. The kit of claim 11, wherein the transparent bottom surface of said DAVU includes a label defining the color of said visualization surface when receiving said chemical reagents and said suspect analyte is present.

15. The kit of claim 3, wherein said hinge is a pair of flexible bands attached at spaced locations to both said SACU and said DAVU.

* * * * *